United States Patent [19]

Matsuda et al.

[11] Patent Number: 4,555,402

[45] Date of Patent: Nov. 26, 1985

[54] PHYSIOLOGICALLY ACTIVE SUBSTANCE K-252, PROCESS FOR PRODUCING SAME AND PHARMACEUTICAL COMPOSITION CONTAINING SAME

[75] Inventors: Yuzuru Matsuda, Koganei; Kazuyuki Iwahashi, Kunitachi; Takao Iida, Hofu; Noriaki Hirayama, Zama; Kozo Asano, Machida; Katsuichi Shuto, Shizuoka; Koji Yamada, Susono; Kunikatsu Shirahata, Komae; Hiroshi Kase, Koganei, all of Japan

[73] Assignee: Kyowa Hakko Kogyo Co. Ltd., Tokyo, Japan

[21] Appl. No.: 640,159

[22] Filed: Aug. 10, 1984

[30] Foreign Application Priority Data

Aug. 12, 1983 [JP] Japan .................................. 58-147471

[51] Int. Cl.$^4$ ........................ A61K 35/74; C12P 1/06
[52] U.S. Cl. .................................... 424/122; 435/169
[58] Field of Search ......................... 424/122; 435/169

[56] References Cited

U.S. PATENT DOCUMENTS 4,169,889 10/1979 Amano et al. ...................... 424/122
4,248,863 2/1981 Arai ..................................... 424/122

Primary Examiner—Jerome D. Goldberg
Attorney, Agent, or Firm—Michael N. Meller

[57] ABSTRACT

A novel physiologically active substance K-252 having an antiallergic action is produced by culturing a microorganism of the genus Nocardiopsis.

3 Claims, 2 Drawing Figures

PHYSIOLOGICALLY ACTIVE SUBSTANCE K-252, PROCESS FOR PRODUCING SAME AND PHARMACEUTICAL COMPOSITION CONTAINING SAME

BACKGROUND OF THE INVENTION

This invention relates to a novel, physiologically active substance, a process for producing the same and a pharmaceutical composition containing the same.

The present inventors have made studies of products produced by many microorganisms obtained in the natural field for the purpose of providing novel, physiologically active substances that can serve as useful medicaments or their intermediates, and, as a result, have found a fact that a physiologically active substance having an antiallergic action is formed in a culture liquor of a microorganism belonging to actinomycetes. By successive isolation and purification of the substance from the culture liquor, and by investigation of its physico-chemical properties, it has been found to be a novel, physiologically active substance. The substance will be hereinafter referred to as "K-252", and its properties, a process for production thereof and a pharmaceutical composition containing it will be described.

SUMMARY OF THE INVENTION

According to the present invention, a novel, physiologically active substance K-252 is produced by culturing a microorganism belonging to the genus Nocardiopsis and being capable of producing K-252 in a culture medium, thereby forming and accumulating K-252 in the culture liquor, and recovering K-252 therefrom. K-252 has antiallergic and antihistamine-releasing activities.

DETAILED DESCRIPTION OF THE INVENTION

Physico-chemical properties of K-252 are given below:

Physico-chemical properties of K-252

State: Light yellow, columnar crystal

Melting point: 262°–273° C. (decomposed)

Specific rotation: $[\alpha]_D^{20} = -23.2°$ C. (C=0.5, CHCl$_3$)

Solubility: Readily soluble in chloroform, acetonitrile, acetone, dioxane, tetrahydrofurane and pyridine; soluble in ethanol, methanol, 1-propanol, ethyl acetate and n-butanol; insoluble in water, 2-propanol, etc.

Color reaction: Positive to reactions with each, iodine and ninhydrin; negative to reaction with ferric chloride and Rydon-Smith reaction.

Figure 1:
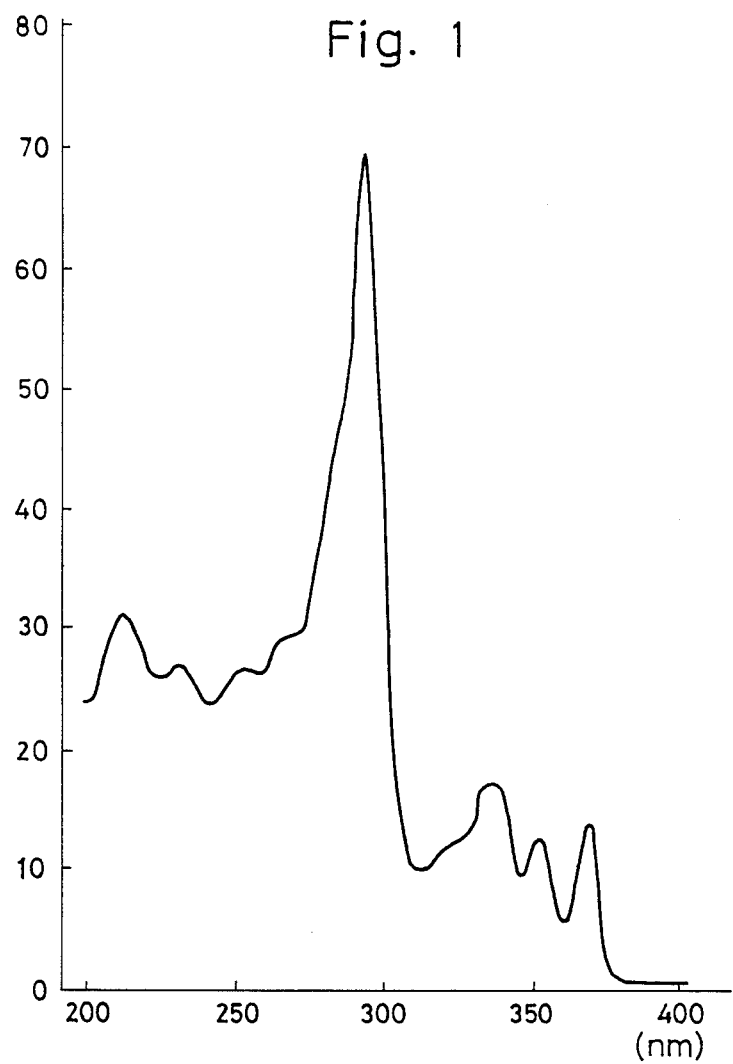
FIG. 1 is an ultraviolet absorption spectrum of K-252 (measured in ethanol).

Ultraviolet absorption spectrum (ethanol): FIG. 1

Figure 2:
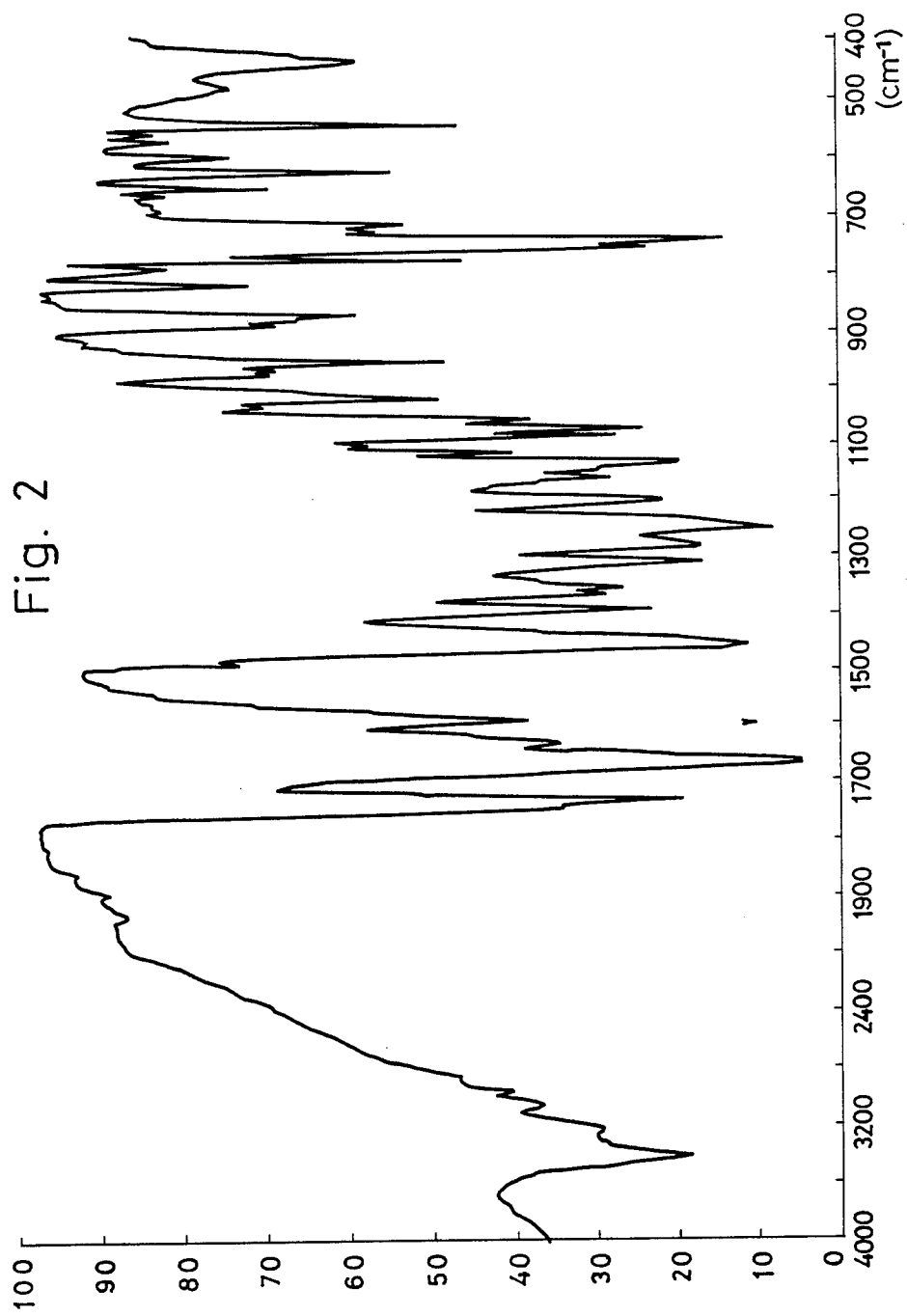
FIG. 2 is an infrared absorption spectrum of K-252 (KBr).

Infrared absorption spectrum (KBr): FIG. 2

Mass Spectrum: The mass spectrum of the present substance gives the following molecule ions and fragment ions: 467, 424, 406, 364, 337, 321.

Elemental analysis: H4.47, C69.08, N8.79% (as found); H4.52, C69.37, N8.98% (as calculated as $C_{27}H_{21}N_3O_5$).

PMR spectrum (CDCl$_3$): δ(ppm) 2.16 (3H, s), 2.81 (1H, dd J=4.9, 14.2), 3.44 (1H, dd, J=7.1, 14.2), 4.08 (3H, s), 4.61 (1H, d, J=17.0), 4.69 (1H, d, J=17.0), 5.46 (1H, brs), 6.79 (1H, dd, J=4.9, 7.1), 7.0–7.6 (6H, m), 7.7–8.0 (2H, m), 8.87 (1H, d, J=7.8).

CMR spectrum (CDCl$_3$): δ(ppm) 22.8, 42.4, 45.9, 53.3, 84.9, 85.7, 99.5, 107.2, 114.2, 114.7, 116.4, 117.8, 119.3, 120.5, 120.7, 122.1, 123.9, 124.9, 125.0, 125.5, 125.8, 129.0, 132.3, 136.8, 140.3, 172.5, 173.5

It has been found from the foregoing data that K-252 is a novel compound.

Rf values of K-252 according to thin layer chromatography with various developing solvents are given in Table 1, where detection is carried out by ultraviolet irradiation at 2537 Å.

TABLE 1

| Silica gel thin layer chromatography of K-252 | |
|---|---|
| Developing solvent | Rf value |
| 1. Chloroform | 0.05 |
| 2. Ethyl acetate | 0.35 |
| 3. Chloroform: methanol = 9:1 (V/V) | 0.6 |
| 4. Methanol | 0.7 |

Thin layer: Kiesel gel 60F$_{254}$ (Merck Co.)

Development: a room temperature, ascending method, 1.5 hours

K-252 is produced as follows. Any microorganism may be used in the present invention so long as it belongs to the genus Nocardiopsis and is capable of producing K-252. An example of the preferred strains is Nocardiopsis sp. K-252. K-252 strain was isolated at Asahi-machi, Machida-shi, Tokyo by the present inventors and has been deposited with Northern Regional Research Laboratory in U.S.A. under the deposit number of NRRL 15532.

Results of observing and testing the morphological characteristics and physiological properties of K-252 strain are given below:

I. MORPHOLOGICAL CHARACTERISTICS

The present strain can moderately grow in synthetic and natural culture media as usually employed. Aerial mycelia are moderately formed and have a white color, and can be formed relatively abundantly in glucose-asparagine agar medium. 10 or more spores are formed in a bent, chain state at the simply branched tip end of the aerial mycelium. The spore is in an ellipsoidal or oval form and 0.4–0.7μ × 1.0–1.5μ in size, and has a smooth surface according to electron-microscopic observations, and neither flagella nor sporangia are observed. Substrate mycelium have a light yellow color, and many branchings and fragmentations are observed. Swellings are also observed at the tip ends of hyphae or halfway thereto.

II. GROWTH STATE ON VARIOUS MEDIA

Growth state, color, etc. of the present strain when allowed to grow on various media are given below, where color is designated according to color classification of Color Harmony Manual (Container Corporation of America).

(1) Sucrose-nitrate agar medium
Growth: moderate
Aerial mycelium: none
Color of substrate mycelium: cream (1½ ca)
Soluble pigment: none (2) Glucose-asparagine agar medium Growth: good
Aerial mycelium: abundant, white (a)
Color of substrate mycelium: light ivory (2 ca)
Soluble pigment: none
(3) Glyceine-asparagine agar medium (ISP No. 5 medium, Difco)
Growth: moderate
Aerial mycelium: moderate, white (a)
Color of substrate mycelium: cream (1½ ca)
Soluble pigment: none
(4) Starch agar medium (ISP No.4 medium, Difco)
Growth: poor-moderate
Aerial mycelium: poor, white (a)
Color of substrate mycelium: parchment (1 cb)
Soluble pigment: none
(5) Tyrosine agar medium (ISP No.7 medium, Difco)
Growth: poor-moderate
Aerial mycelium: moderate, white (a)
Color of substrate mycelium: cream (1½ ca)
Soluble pigment: none
(6) Nutrient agar medium
Growth: moderate
Aerial mycelium: moderate, white (a)
Color of substrate mycelium: light ivory (2 ca)-light wheat (2 ea)
Soluble pigment: none
(7) Yeast-Malt agar medium (ISP No.2 medium, Difco)
Growth: good
Aerial mycelium: moderate, white (a)
Color of substrate mycelium: bamboo (2 gc)-gold (2 lc)
Soluble pigment: very light swash yellow (2 ia)
(8) Oatmeal agar medium
Growth: poor
Aerial mycelium: poor, white (a)
Color of substrate mycelium: light ivory (2 ca)
Soluble pigment: none
(9) Peptone-yeast-iron agar medium
Growth: moderate
Aerial mycelium: none
Color of substrate mycelium: colonial yellow (2 ga)-cream (1½ ca)
Soluble pigment: none

III. PHYSIOLOGICAL PROPERTIES

Plysiological properties of K-252 strain are given below, where results of observation after culturing at 28° C. for 3 weeks are shown for other than the growth temperature range and actions on milk and cellulose, and the result of the growth temperature range is that after culturing for two days, and the results on milk and cellulose are those after culturing at 28° C. for one month.

(1) Assimilability of carbon source: The strain can assimilate D-glucose, inositol and L-rhamnose, but cannot assimilate L-arabinose, D-xylose, D-fructose, sucrose, raffinose and D-mannitol.

(2) Gelatin liquefaction: negative (3) Clotting and peptonization of defatted milk: clotting action being negative, but peptonization action being positive (4) Cellulose decomposition: negative (5) Starch hydrolysis: positive (6) Growth temperature range: 10°–38° C.; optimum 22°–33° C.

(7) Melanin-like pigment formation: negative

K-252 strain is a mesophil capable of forming spore chains in long aerial mycelium, where breaking of substrate mycelium is observed, and is concluded to be a strain belonging to the genus Nocardiopsis of actinomycetes on the basis of the results that meso-diaminopimelic acid is contained according to the analysis of cell wall and that neither arabinose nor madurose is contained according to the analysis of cell sugars.

For culturing the present K-252-producing strain, the ordinary procedure for culturing actinomycetes can be used generally.

Either a synthetic or natural medium may be used so long as it properly contains a carbon source and a nitrogen source, and, if necessary, minerals and other nutrients.

As a carbon source, glucose, starch, mannose, fructose, sucrose, molasses, etc. can be used alone or in combination. Furthermore, hydrocarbons, alcohols, organic acids, etc. can be used, depending on the assimilability of the strain.

As a nitrogen source, nitrogen-containing compounds such as ammonium chloride, ammonium sulfate, urea, ammonium nitrate, sodium nitrate, etc., and nitrogen-containing natural products such as peptone, meat extract, yeast extract, dry yeast, corn steep liquor, soybean meal, casamino acid, soluble vegetable protein, etc. can be used alone or in combination. If necessary, inorganic salts such as sodium chloride, potassium chloride, calcium carbonate, phosphate, etc. can be further added thereto, and also organic or inorganic substances capable of promoting the growth of the present strain or production of K-252 can be appropriately added thereto.

Most preferable culturing procedure is liquid culturing, particularly submerged stirring culturing. It is desirable to conduct culturing at a temperature of 25°–40° C. and around a neutral pH. Liquid culturing usually for 6–7 days can form and accumulate K-252 in the culture liquor. When the accumulation in the culture liquor reaches a maximum, the culturing is discontinued, and the cells are removed by filtration. The desired substance is isolated from the filtrate of culture liquor and the cells, and purified.

For isolation and purification of K-252 from the filtrate and the cells, the ordinary procedure for isolating microorganism metabolic products can be used. That is, K-252 can be purely recovered through an appropriate combination or repetitions of adsorption and desorption by active carbon, Diaion HP-10 (adsorbent resin, Mitsubishi Kasei Co.), etc., silica gel column chromatography, silanized silica gel column chromatography, Sephadex LH-20 (ion exchanger, Pharmacia Fine Chemicals Co.) column chromatography, etc. One example of it is given below:

The filtrate of culture liquor is passed through a column filled with Diaion HP-10, without pH adjustment, to absorb K-252 onto the resin. The column is washed with water and further thoroughly with a 30% aqueous acetone solution, and then subjected to elution with 100% acetone. Fractions containing K-252 are collected, and subjected to evaporation under reduced pressure to remove acetone therefrom. The residue is extracted with ethyl acetate, and the ethyl acetate layer is concentrated under reduced pressure.

Then, the residue is dissolved in a small amount of chloroform, and the solution is charged on the upper end of a silica gel column packed using chloroform to make adsorption on silica gel. Then, the column is thoroughly washed with chloroform, and subjected to elution with chloroform:methanol=98:2 (V/V). Fractions containing K-252 are collected, and subjected to evaporation under reduced pressure to remove the solvent therefrom, up to dryness. The residue is dissolved in a small amount of chloroform, and methanol is added thereto. The solution is allowed to stand at 5° C. to obtain light yellow columnar crystals.

In the isolation and purification of K-252 from the cells, K-252 can be extracted with a hydrous solvent such as an aqueous methanol solution, an aqueous acetone solution, etc., and in better yield with an anhydrous solvent. A K-252 solution extracted, for example, with methanol from the cells is concentrated and subjected to evaporation under reduced pressure to remove methanol therefrom, and then to extraction with ethyl acetate. Then, K-252 can be purely isolated in the same procedure as in the purification procedure for isolating K-252 from the filtrate of culture liquor.

Detection of K-252 in the above purification steps is carried out by thin layer chromatography using silica gel containing a fluorescentizing agent, and they by iodine reaction or by ultraviolet irradiation at 2537 Å.

K-252 has antiallergic and antihistamine-releasing activities. Thus, according to a further feature of the present invention, there is provided a pharmaceutical composition, comprising, as active ingredient, an effective amount of K-252 usually in association with at least one pharmaceutically acceptable carrier or excipient.

Dosage for these purposes depends upon the desired healing effect, way of administration, healing period, age, body weight, etc., and usually is 0.1–4 mg/kg per day for an adult as K-252 through oral or parenteral route (for example, injection, application, inhalation, etc.). K-252 can be administered as such, but generally administered in the form of tablets, pills, powder, granules, capsules, depository, injection, etc. Conventional pharmaceutically acceptable carriers can be used for medical compositions of this invention and include lactose, dextrose, sucrose, sorbitol, mannitol, glucose, cellulose, cyclodextrin, talc, starch, methylcellulose, gelatin, arabic gum, polyethylene glycol, carboxymethylcellulose, hydroxypropylcellulose, sodium benzoate, sodium hydrogen sulfite, aluminum stearate, magnesium stearate, mineral oil, vegetable oil, white vaseline, liquid paraffin, etc., and can be appropriately selected in view of the kind of preparations. The present composition can contain 0.01–85 weight percent of K-252.

The present invention will further be described below, referring to examples and experimental examples.

EXAMPLE 1

As a seed microorganism, Nocardiopsis sp. K-252 (NRRL 15532) is used, and as a first seed medium, a medium containing 0.5 g/dl glucose, 3 g/dl soluble starch, 3 g/dl soybean meal, 0.5 g/dl corn steep liquor, 0.5 g/dl yeast extract and 0.3 g/dl calcium carbonate (pH 7.2–7.4 before the sterilization) is used. One loopful of the seed microorganism is inoculated in 14 ml of the seed medium in a 50 ml-large test tube, and cultured with shaking at 30° C. for 3 days.

Then, 4 ml of the seed culture liquor is inoculated in 40 ml of a second seed medium in a 300 ml-Erlenmeyer flask.

The second seed medium has the same composition as that of the first seed medium. Second seed culturing is carried out at 30° C. for 3 days. Then, 40 ml of the second seed culture liquor is inoculated in 300 ml of a third seed medium in a 2 l-Erlenmeyer flask with baffles. The third seed medium has the same composition as that of the first seed medium. Third seed culturing is carried out at 30° C. for 4 days. Then, 900 ml of the third seed culture liquor is inoculated in 18 l of main fermentation medium in a 30 l-stainless steel jar fermenter. The main fermentation medium has the same composition as that of the first seed medium. The main fermentation culturing is carried out at 30° C. for 7 days by aeration-stirring (300 rpm, aeration rate 18 l/min.).

Then, 18 l of the thus obtained fermentation liquor is continuously centrifuged (15000 rpm), and the supernatant is passed through a column filled with 2 l of Diaion HP-10 to adsorb K-252 onto the resin. Then, the column is washed with 6 l of water, and then with 6 l of a 30% aqueous acetone solution, and elution is carried out with 4 l of acetone.

All of the eluates are collected and concentrated to 530 ml, and extracted with 1.6 l of ethyl acetate. The ethyl acetate layer is dehydrated with anhydrous sodium sulfate, and concentrated to dryness, whereby about 4.9 g of dark yellow, oily product is obtained. The oily product is dissolved in 10 ml of chloroform, and the soluton is charged on the upper end of 150 ml of silica gel column (Wako-gel, made by Wako Junyaku Co.) packed using chloroform to make adsorption onto the silica gel. After washing with 1.2 l of chloroform, elution is carried out with chloroform:methanol=98:2 (V/V). The eluate is collected in 15 g fractions, and K-252 is eluted into fraction Nos. 81–151. These fractions are collected and concentrated to dryness under reduced pressure, whereby about 1.4 g of crude powder is obtained. The crude powder is dissolved in 3.5 ml of chloroform, and 35 ml of methanol is added thereto. The solution is allowed to stand at 5° C. for about 2 days, whereby 840 mg of light yellow columnar crystal is obtained.

Separation from cells will be described below:

At first, 4 l of methanol is added to 900 g of the cells separated by continuous centrifugation, and the mixture is stirred and then allowed to stand at a room temperature for 24 hours.

The cells are separated from the mixture by filtration, and about 4 l of the methanol extract is concentrated to about 240 ml under reduced pressure, and extracted with 1.1 l of ethyl acetate. The ethyl acetate layer is dehydrated with anhydrous sodium sulfate and concentrated to dryness, whereby about 2.0 g of dark yellow, oily product is obtained. The oily product is dissolved in 5 ml of chloroform, and the solution is charged on the upper end of 100 ml of silica gel column Wakogel, made by Wako Junyaku Co.) packed using chloroform to make adsorption on the silica gel. After washing with 600 ml of chloroform, elution is carried out with chloroform:methanol=98:2 (V/V). Eluate is collected in 15 g of fractions, and K-252 is eluted into fraction Nos. 41–73. These fractions are collected and concentrated to dryness under reduced pressure, whereby about 420 mg of crude powder is obtained. The crude powder is dissolved in 1.1 ml of chloroform, and 11 ml of methanol is added thereto. The mixture is allowed to stand at 5° C. for about 2 days, whereby about 250 mg of light yellow columnar crystal is obtained. In the foregoing purification steps, detection of K-252 is carried out by thin layer chromatography using silica gel containing a fluorescent agent (Kiesel gel 60 $F_{252}$, Merck Co.) and then by iodine reaction or by ultraviolet irradiation at 2537 Å.

EXAMPLE 2 TABLETS

A 10% hydroxypropylcellulose solution is added to a mixture consisting of 100 g of K-252, 40 g of lactose, 18 g of corn starch and 10 g of carboxymethylcellulose calcium, and the mixture is kneaded. The mixture is then granulated by an extrusion granulator with 1.0 mm screen, and the granules are dried at 60° C. The dried granules are screened on a 16-mesh sieve, and magnesium stearate is added to the granules to prepare tabletting granules. According to the ordinary procedure, tablets, 8 mm in size, each containing 100 mg of K-252 in one tablet (170 mg), are prepared.

EXAMPLE 3 CAPSULES

A 10% hydroxypropylcellulose solution is added to a mixture consisting of 50 g of K-252, 80 g of lactose and 38 g of potato starch, and the mixture is kneaded. The mixture is granulated in the same manner as in Example 2, and after addition of magnesium stearate, capsules each containing 50 mg of K-252 in one capsule (170 mg) are prepared according to an ordinary procedure.

EXAMPLE 4 SOFT CAPSULES

At first, 10 g of K-252 is dissolved in 100 g of soybean oil, and the solution is filled into capsules, each containing 10 mg of K-252, according to the ordinary procedure, to prepare soft capsules.

EXAMPLE 5 OINTMENT

At first, 20 g of K-252 is mixed with a mixture of white vaseline and liquid paraffin to prepare an ointment containing 100 mg/g of K-252.

EXPERIMENTAL EXAMPLE 1

Action on homologous passive cutaneous anaphylaxis (homologous PCA) in rats:

(1) PREPARATON OF ANTI-EGG WHITE ALBUMIN RAT SERUM

Anti-egg white albumin rat serum was prepared according to Stotland and Share method [Canad. J. Physiol. Pharmacol. 52 1114 (1974)]. That is, 1 mg of egg white albumin was mixed with 20 mg of aluminum hydroxide gel and 0.5 ml of a mixture of pertussis vaccine, diphtheria vaccine and tetanus vaccine. The mixture was intracutaneously administered in 4 portions into soles of rats with body weights of 180–220 g. Blood was collected from carotid artery 14 days thereafter, and serum was separated from the blood and freeze-reserved at $-80°$ C. Titer of homologous passive cutaneous anaphylaxis for 48 hours of the antiserum was 1:32.

(2) HOMOLOGOUS PASSIVE CUTANEOUS ANAPHYLAXIS FOR 48 HOURS

Into each of the backs of rats with body weights of 140–160 g were intracutaneously injected 0.05 ml of egg white albumin rat serum diluted 8-fold with physiological saline solution to make the animals passively sensitized. Then, 48 hours thereafter, 0.5 ml of 1% Evans' blue containing 2 mg of antigen egg white albumin was administered into the tail vein. Thirty minutes thereafter, the animals was sacrificed by exsanguination. The exudated dye at each site was extracted by the method of Katayama et al. [Microbiol. Immunol. 22, 89 (1978)] and quantified by spectrometry. That is, the blue-dyed parts were incubated in 1N KOH at 37° C. for 24 hours, and extracted with 0.6N phosphoric acid-acetone mixture, and absorbancy at the wavelength of 620 μm was measured by a spectrophotometer, and a calibration curve prepared in advance was used, whereby amount of dye leaked was quantitatively determined.

(3) TEST RESULTS

TABLE 2

| Medicament (a) | Body weight (g) | Amount of dye leaked (μg/site) | Suppressing ratio (%) (b) |
|---|---|---|---|
| Control group (0.3% CMC administered) | 148 | 41.7 | |
| | 142 | 50.9 average | |
| | 149 | 38.8 (43.8) | |
| K-252 10 mg/kg P.O. | 155 | 25.7 | 41.3 |
| | 147 | 30.8 | 29.7 |
| | 148 | 19.1 | 56.4 |
| K-252 1 mg/kg P.O. | 146 | 30.6 | 30.1 |
| | 146 | 35.7 | 18.5 |
| | 152 | 32.6 | 25.6 |

(a): Medicament was orally administered one hour before the antigen administration.
(b): Calculated from the pigment leakage of individuals on the basis of the average of control group.

When 1 and 10 mg/kg of K-252 were orally administered, amount of dye leaked was found to be reduced, as compared with the control group, as shown in Table 2.

EXPERIMENTAL EXAMPLE 2

Influence on histamine liberation from exudated cells in rat abdominal cavities.

(1) PREPARATION OF RAT ISOLATED PERITONEAL EXUDATE CELLS AND HISTAMINE LIBERATION

Rats with body weights of 150–180 g were killed under ether anesthesia by exsanguination, and mast cell medium prepared according to Sullivan et al procedure [J. Immunol. 114, 1473 (1975)] (hereinafter abbreviated as MCM, composition: 150 mM NaCl, 3.7 mM KCl, 3 mM $Na_2HPO_4$, 3.5 mM $KH_2PO_4$, 1 mM $CaCl_2$, 5.6 mM glucose, 0.1% bovine serum albumin, 10 U/ml heparin) was injected intraperitoneally into the animals at 6 ml/animal. The abdominal parts were massaged for two minutes, and then cut open to sample exudated solution in the abdominal cavities. The exudated solution collected from 6 rats was centrifuged at 100 G for 5 minutes at 4° C., and the precipitate was mixed with an appropriate amount of water-cooled MCM, and washed three times to prepare a cell suspension (peritoneal exudate cells, hereinafter abbreviated as "PEC") whose ultimate mast cells can amount to about $3 \times 10^4$ cells/ml. Identification of mast cells was carried out by staining intracellular granules by 0.05% toluidine blue. Then, 1 ml of the thus obtained PEC was preincubated at 37° C. for 10 minutes, and then admixed with 0.1 ml of test solutions at various concentrations and incubated for 10 minutes. Then, the incubated mixtures were further admixed with 0.1 ml each of 100 μg/ml phosphatidyl-L-serine and 1000 μg/ml concanavalin A, and further incubated for 15 minutes. The reaction was discontinued by adding 3 ml of ice-cooled physiological saline solution thereto, and the mixture was centrifuged at 1100 G for 10 minutes at 4° C. to obtain the supernatant and the residue. Histamine content of the supernatant and the residue was measured by fluorometry according to Komatsu's procedure [Jpn. J. Allergol. 27, 67 (1978)].

Percent histamine liberation was defined by a percentage of histamine content in the supernatant to total histamine content in the cells. Percent suppression of test solution on histamine liberation was calculated according to the following formula:

$$\text{Percent suppression on liberation (\%)} = \left[1 - \frac{\text{Histamine liberation in the presence of medicament} - \text{Spontaneous liberation}}{\text{Histamine liberation in the absence of medicament} - \text{Spontaneous liberation}}\right] \times 100$$

(2) TEST RESULTS

TABLE 3

| Concentration of test solution (μg/ml) | Percent suppression on histamine liberation (%) |
|---|---|
| 0.1 | 57 |
| 1 | 98 |
| 10 | 100 |

As shown in Table 3, K-252 suppressed histamine liberation in a concentration dependent manner.

What is claimed is:

1. A physiologically active substance K-252 having the following physico-chemical properties:

State: Light yellow, columnar crystal

Melting point: 262°–273° C. (decomposed)

Specific rotation: $[\alpha]_D^{20} = -23.2°$ C. (C=0.5, CHCl$_3$)

Solubility: Readily soluble in chloroform, acetonitrile, acetone, dioxane, tetrahydrofuran and pyridine; soluble in ethanol, methanol, 1-propanol, ethyl acetate and n-butanol; insoluble in water, 2-propanol, etc.

Color reaction: Positive to reactions with each, iodine and ninhydrin; negative to reaction with ferric chloride and Rydon-Smith reaction Ultraviolet absorption spectrum (ethanol): FIG. 1

Infrared absorption spectrum (KBr): FIG. 2

Mass Spectrum: The mass spectrum of the present substance gives the following molecule ions and fragment ions: 467, 424, 406, 364, 337, 321

Elemental analysis: H4.47, C69.08, N8.79% (as found); H4.52, C69.37, N8.98% (as calculated as $C_{27}H_{21}N_3O_5$)

PMR spectrum (CDCl$_3$): δ(ppm) 2.16 (3H, s), 2.81 (1H, dd, J=4.9, 14.2), 3.44 (1H, dd, J=7.1, 14.2), 4.08 (3H, s), 4.61 (1H, d, J=17.0), 4.69 (1H, d, J=17.0) 5.46 (1H, brs), 6.79 (1H, dd, J=4.9, 7.1) 7.0–7.6 (6H, m), 7.7–8.0 (2H, m), 8.87 (1H, d, J=7.8)

CMR spectrum (CDCl$_3$): δ(ppm) 22.8, 42.4, 45.9, 53.3, 84.9, 85.7, 99.5, 107.2, 114.2, 114.7, 116.4, 117.8, 119.3, 120.5, 120.7, 122.1, 123.9, 124.9, 125.0, 125.5, 125.8, 129.0, 132.3, 136.8, 140.3, 172.5, 173.5.

2. A process for producing substance K-252 as defined in claim 1, characterized by culturing the microorganism Nocardiopsis sp. K-252 in a culture medium, thereby forming and accumulating a sufficient amount of substance K-252 in the culture liquor, and recovering K-252 from the culture liquor.

3. A pharmaceutical composition comprising as active ingredient an antiallergenically effective amount of substance K-252 as defined in claim 1 in association with at least one pharmaceutically acceptable carrier or excipient.

* * * * *